United States Patent
Grompone et al.

(10) Patent No.: US 9,855,304 B2
(45) Date of Patent: *Jan. 2, 2018

(54) *LACTOBACILLUS RHAMNOSUS* STRAIN FOR REDUCING BODY FAT ACCUMULATION

(71) Applicants: COMPAGNIE GERVAIS DANONE, Paris (FR); BIOPOLIS, S.L., Paterna (ES)

(72) Inventors: Gianfranco Grompone, Paris (FR); Daniel Ramon Vidal, Valencia (ES); Patricia Martorell Guerola, Valencia (ES); Salvador Genoves Martinez, Valencia (ES); Josefa Ortiz Serrano, Valencia (ES); Silvia Llopis Pla, Valencia (ES); Nuria Gonzalez Martinez, Valencia (ES)

(73) Assignees: Compagnie Gervais Danone, Paris (FR); Biopolis S.L., Paterna (ES)

( * ) Notice: Subject to any disclaimer, the term of this patent is extended or adjusted under 35 U.S.C. 154(b) by 215 days.

This patent is subject to a terminal disclaimer.

(21) Appl. No.: 14/442,031

(22) PCT Filed: Nov. 12, 2012

(86) PCT No.: PCT/IB2012/056344
§ 371 (c)(1),
(2) Date: May 11, 2015

(87) PCT Pub. No.: WO2014/072771
PCT Pub. Date: May 15, 2014

(65) Prior Publication Data
US 2015/0283186 A1   Oct. 8, 2015

(51) Int. Cl.
| | |
|---|---|
| A01N 63/00 | (2006.01) |
| A61K 35/747 | (2015.01) |
| A23C 9/123 | (2006.01) |
| A23L 33/135 | (2016.01) |
| A61K 35/00 | (2006.01) |

(52) U.S. Cl.
CPC .......... *A61K 35/747* (2013.01); *A23C 9/1234* (2013.01); *A23L 33/135* (2016.08); *A23V 2002/00* (2013.01); *A23Y 2220/73* (2013.01); *A61K 2035/115* (2013.01)

(58) Field of Classification Search
None
See application file for complete search history.

(56) References Cited

U.S. PATENT DOCUMENTS

| 7,001,756 B1 | 2/2006 | Hsu et al. |
|---|---|---|
| 2005/0186189 A1 | 8/2005 | Hsu et al. |

FOREIGN PATENT DOCUMENTS

| EP | 1918373 A1 | 5/2008 |
|---|---|---|
| EP | 2022502 A1 | 2/2009 |
| EP | 2216035 A1 | 8/2010 |
| JP | 2008-507991 A | 3/2008 |
| JP | 2010-535731 A | 11/2010 |
| JP | 2011-206057 A | 10/2011 |
| WO | 2006/019222 A1 | 2/2006 |
| WO | 2009/021824 A1 | 2/2009 |
| WO | 2011/083354 A1 | 7/2011 |

OTHER PUBLICATIONS

Pi-Sunyer, Postgrad Med., 121(6): 21-33 (2009).*
Must et al., JAMA, 282:1523-1529 (1999).*
Lee et al., "Human originated bacteria, *Lactobacillus rhamnosus* PL60, produce conjugated linoleic acid and show anti-obesity effects in diet-induced obese mice," Biochimica et Biophysica Acta, 1761: 736-744 (2006).
International Search Report and Written Opinion issued in corresponding International Patent Application No. PCT/IB2012/056344 dated May 7, 2013.

* cited by examiner

Primary Examiner — Thomas J Visone
(74) Attorney, Agent, or Firm — Morgan, Lewis & Bockius LLP

(57) ABSTRACT

The invention relates to the use of *Lactobacillus rhamnosus* strain CNCM I-3690 for reducing body fat accumulation and treating disorders resulting therefrom, such as overweight, obesity, and obesity-related disorders.

4 Claims, 1 Drawing Sheet

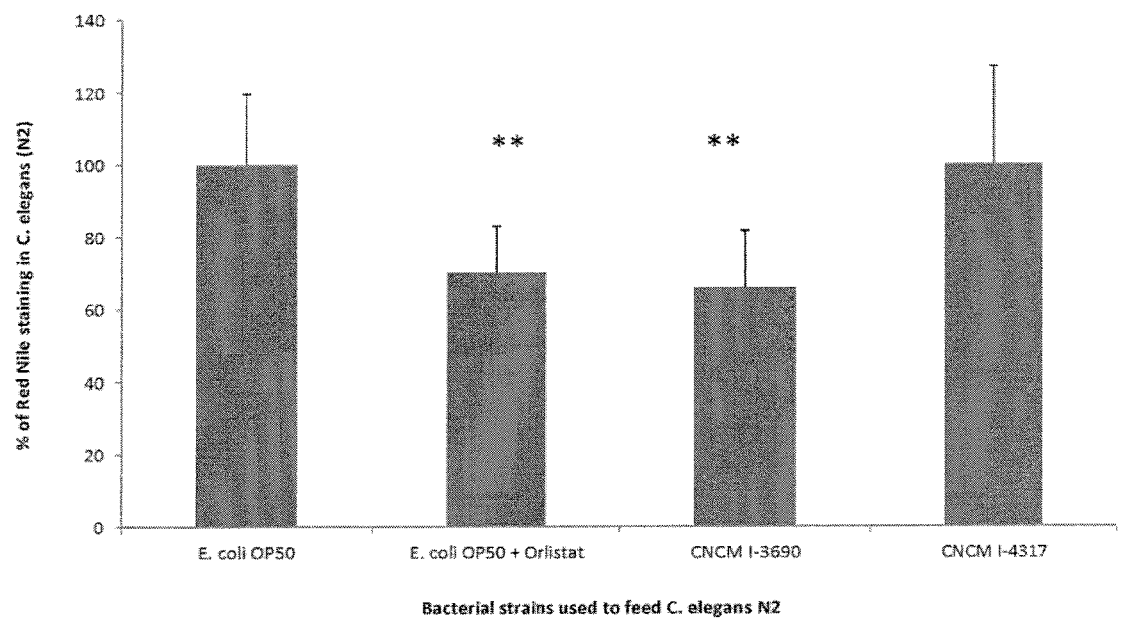

LACTOBACILLUS RHAMNOSUS STRAIN FOR REDUCING BODY FAT ACCUMULATION

The invention relates to the field of probiotics, and more specifically to their use for regulating lipid metabolism.

Lipid metabolism plays an essential part in energy homeostasis. Energy from food can be stored as lipid reserves which can be used when necessary to meet the body's energy needs. An excess caloric intake over caloric expenditure induces weight gain due to fat accumulation in the body, leading to overweight and in the longer term to obesity. A body mass index (BMI) greater than or equal to 25 is considered overweight and a BMI greater or equal to 30 is defined as obesity.

Since obesity is an important risk factor for major diseases including hypertension, type II diabetes, cardiovascular diseases, liver diseases and some cancers, it is rapidly becoming a major public health problem. The number of obese people worldwide has more than doubled since 1980. In 2008, more than 1.4 billion adults, 20 and older, were overweight. Of these over 200 million men and nearly 300 million women were obese.

It is generally acknowledged that one of the primary causes of the current frequency of obesity and related metabolic disorders is the combination of reduced physical activity in the daily lives, with the western-style diet, rich in high-fat and high-sucrose foods.

However, differences in fat accumulation and body weight among individuals are also correlated with other factors, such as genetic background, health conditions, medical treatments, age, or lack of sleep.

Among these factors, the gut microbiota is the focus of increasing interest. Numerous investigations in recent years have shown that obesity and obesity-related metabolic disorders are associated with changes in the composition of the intestinal microbiota (for review see TREMAROLI & BACKHED, Nature, 489, 242-9, 2012; MARIK, Front Endocrinol (Lausanne), 3, 87, 2012; BURCELIN, Physiology, 27, 300-7, 2012).

Therefore, it has been suggested that manipulation of gut microbiota using prebiotics, probiotics, or synbiotics, may help to reduce obesity and obesity-related metabolic disorders (MALLAPPA et al., Indian J Endocrinol Metab, 16, 20-7, 2012; DELZENNE et al., Nat Rev Endocrinol, 7, 639-46, 2011)

Some probiotic strains have been reported to decrease fat accumulation and/or obesity-related metabolic disorders. LEE et al. (Biochim Biophys Acta, 1761, 736-44, 2006) have shown that *Lactobacillus rhamnosus* strain PL60, which produces conjugated linoleic acid has anti-obesity effects in diet-induced obese mice; *Lactobacillus gasseri* SBT2055 has been shown to reduce abdominal adiposity and body weight in human adults (KADOOKA et al., Eur J Clin Nutr, 64, 636-43, 2010), and *Lactobacillus gasseri* BNR17 has been shown to reduce the gain in body weight in rats fed a high-carbohydrate diet (KANG et al., J Microbiol, 48, 712-4, 2010). ANDREASEN et al. (Br J Nutr, 104, 1831-8, 2010) reported an improvement of insulin resistance upon administration of *Lactobacillus acidophilus* NCFM. *Lactobacillus plantarum* strain No. 14 was shown to reduce adipocyte size in mice fed high-fat diet (TAKEMURA et al., Exp Biol Med (Maywood), 235, 849-56, 2010). ARONSSON et al. (PLoS One, 5, 2010) reported that *Lactobacillus paracasei* ssp *paracasei* strain F19 can decrease fat storage by increasing the expression of angiopoietin-like 4 protein (ANGPTL4). M A et al. (J Hepatol, 49, 821-30, 2008) reported that probiotics VSL#3 improve high fat diet-induced hepatic steatosis and insulin resistance by increasing hepatic NKT cells. Modulation of the murine microbiome by *Lactobacillus rhamnosus* GG and *Lactobacillus sakei* NR28, with a concomitant anti-obesity effect, was reported by J I et al. (Benef Microbes, 3, 13-22, 2012). A N et al. (Lipids Health Dis, 10, 116, 2011) described the antiobesity and lipid-lowering effects of a mixture of Bifidobacterial strains (*B. pseudocatenulatum* SPM 1204, *B. longum* SPM 1205, and *B. longum* SPM 1207) in high fat diet-induced obese rats. PCT application WO2007/043933 proposes the use of *Lactobacillus casei* F19, *Lactobacillus acidophilus* NCFB 1748 or *Bifidobacterium lactis* Bb12 for reducing food intake and fat deposition, and preventing or treating obesity and insulin insensitivity.

The effects of these different probiotics are strain-specific, and appear to be mediated by different mechanisms. Thus, a need remains for other probiotic strains that can be used for controlling the development of overweight and obesity and metabolic diseases associated therewith.

The inventors have undertaken to test probiotic strains for their ability to modulate lipid metabolism, using *Caenorhabditis elegans* as an in vivo model.

Many genes involved in the fat regulatory pathways are highly conserved between *C. elegans* and mammals (ASHRAFI et al., Nature, 421, 268-72, 2003), and therefore it has become a popular model for studying the mechanisms involved in obesity (ASHRAFI, WormBook, 1-20, 2007; JONES & ASHRAFI, Dis Model Mech, 2, 224-9, 2009).

In addition, *C. elegans* stores fat in the form of lipid droplet in their intestinal and in their hypodermal cells. These fat stores can be easily visualized and quantified in intact animals after staining with fluorescent dyes such as Nile Red, making possible to easily evaluate the effect of tested products on the accumulation of body fat.

The inventors have found that, among the probiotic strains tested, one strain of *Lactobacillus rhamnosus*, strain CNCM I-3690, decreased lipid storage to the same extent as orlistat, which is a reversible gastrointestinal lipase inhibitor preventing absorption of dietary fat, and is broadly used as a medication for the management of obesity.

This effect is strain-specific, since it was not observed with another probiotic strain of *Lactobacillus rhamnosus*, strain CNCM I-4317 (described in PCT application WO 2011/148355).

Strain CNCM I-3690 was deposited according to the Budapest Treaty at Collection nationale de cultures de micro-organismes (Institut Pasteur, 25-28, rue de Docteur Roux, 75724 Paris Cedex 15) ("CNCM") on Nov. 19, 2006. It is disclosed in PCT application WO 2009/122042, which reports its anti-microbial and immunomodulatory properties. This strain has also anti-oxidant properties, which are described in PCT application WO 2011/083354.

Therefore, an object of the present invention is the use of *Lactobacillus rhamnosus* strain CNCM I-3690, or of a composition containing said strain, for reducing body fat accumulation in a subject.

In particular, the present invention encompasses *Lactobacillus rhamnosus* strain CNCM I-3690 or a composition containing said strain, for use in the treatment, treating, prevention, or alleviation of a condition resulting from excessive body fat accumulation.

Examples of conditions resulting from excessive body fat accumulation are overweight, obesity, and obesity-related disorders, such as type 2 diabetes, non-alcoholic fatty liver disease (NAFLD), hypertension, etc.

*Lactobacillus rhamnosus* strain CNCM I-3690 can be used in the form of whole bacteria which may be living or not. Alternatively, it can be used in the form of a bacterial lysate or in the form of bacterial fractions; the bacterial fractions suitable for this use can be chosen, for example, by testing their properties on lipid storage in *C. elegans*.

The present invention also provides a method for treating, alleviating, or preventing excessive body fat accumulation in a subject in need thereof, wherein said method comprises administrating to said subject *Lactobacillus rhamnosus* strain CNCM I-3690, or a composition containing said strain.

The compositions for use in the present invention can be in any form suitable for administration, in particular oral administration. This includes for instance solids, semi-solids, liquids, and powders. Liquid composition are generally preferred for easier administration, for instance as drinks.

When the bacteria are in the form of living bacteria, the composition may typically comprise $10^5$ to $10^{13}$ colony forming units (cfu), preferably at least $10^6$ cfu, more preferably at least $10^7$ cfu, still more preferably at least $10^8$ cfu, and most preferably at least $10^9$ cfu per g dry weight of the composition. In the case of a liquid composition, this corresponds generally to $10^4$ to $10^{12}$ colony forming units (cfu), preferably at least $10^5$ cfu, more preferably at least $10^6$ cfu, still more preferably at least $10^7$ cfu, and most preferably at least $10^9$ cfu/ml.

Preferred compositions for use in the present invention are nutritional compositions, including food products and in particular dairy products. These nutritional compositions also include food supplements, and functional food. A "food supplement" designates a product made from compounds usually used in foodstuffs, but which is in the form of tablets, powder, capsules, potion or any other form usually not associated with aliments, and which has beneficial effects for one's health. A "functional food" is an aliment which also has beneficial effects for one's health. In particular, food supplements and functional food can have a physiological effect—protective or curative—against a disease, for example against a chronic disease.

Other examples of compositions suitable for use in the present invention are pharmaceutical or cosmetic compositions.

The compositions of the invention can also comprise, besides strain CNCM I-3690 one or more other strain(s) of lactic acid bacteria, probiotic or not, for instance one or more bacterial strain(s) selected from the genera *Lactobacillus, Lactococcus, Streptococcus,* and *Bifidobacteria*. In particular, this (these) other strain(s) can include one or more strain(s) of *Streptococcus thermophilus*, and/or one or more strain(s) of *Lactobacillus bulgaricus*.

The present invention will be understood more clearly from the further description which follows, which refers to an example illustrating the effect of the bacterial strain CNCM I-3690 on lipid storage.

EXAMPLE: *LACTOBACILLUS RHAMNOSUS* CNCM I-3690 INHIBITS TOTAL FAT DEPOSIT IN *C. ELEGANS*

The effect of the *Lactobacillus rhamnosus* strains CNCM I-3690 and CNCM I-4317 on *C. elegans* lipid inclusions was studied via fluorescence measurement in Red Nile stained worms.

The *Lactobacillus rhamnosus* strains were grown in MRS medium and recovered in the logarithmic phase growth (OD600=1.5).

Experiments were carried out with the wild type strain N2 of *C. elegans*. Worms were synchronized by isolating eggs from gravid adults, hatching the eggs overnight in M9 medium (10 vol % MRS, fluorodexouridine 110 ug/ml) plus 5 ug/ml cholesterol and isolating $L_1$-stage worms in the wells of a microtiter plate. The worms were grown without shaking during three days at 25° C. and 80-85% relative humidity. These larvae were transferred to plates comprising M9 medium plus cholesterol and incubated for 3 days at 25° C. 80-85% humidity while undergoing control or experimental feeding. At least 50 worms were present per well.

The worms were fed with the standard feed *E. coli* OP50, *E. coli* OP50 with orlistat as a positive control, *L. rhamnosus* CNCM I-3690, or *L. rhamnosus* CNCM I-4317. All the bacteria were used at a concentration of $4\times10^6$ cfu/ml. Orlistat was used at a concentration of 6 µg/ml. Kanamycin, 30 µg/ml, was added to prevent growth of *E coli* OP50 or of the *L. rhamnosus* strains during the assay.

Red Nile (0.05 µg/mL, Sigma, St. Louis, USA) was added to the plates at the beginning of the feeding, at a concentration of 0.05 µg/ml.

Fat deposit was measured by fluorescence quantification (λ excitation=480 nm; λ emission=571 nm) using a VersaFluor™ Fluorometer System (Bio-Rad, Hercules, USA). A total of 180 worms per condition were analyzed. Experiments were carried out in triplicate.

The results are shown in FIG. 1, which represents the percent of Red Nile staining for each condition tested: ** p-value=0.001.

These results show that while strain CNCM I-4317 has no effect on fat deposit when compared to the standard feed *E. coli* OP50, strain CNCM I-3690 reduced lipid inclusions of 34%, which is comparable to the reduction in lipid inclusions observed with orlistat.

The invention claimed is:

1. A method for reducing body fat accumulation in a subject, comprising administering to the subject *Lactobacillus rhamnosus* strain deposited at the collection nationale de cultures de microorganisms (CNCM) with the accession number 1-3690, wherein the subject has a body mass index (BMI) greater than or equal to 25.

2. The method of claim 1, wherein said strain is contained in an orally administrable composition.

3. The method of claim 2, wherein said composition is a food product or a food supplement.

4. The method of claim 3, wherein said food product is a fermented dairy product.

* * * * *